(12) United States Patent
Taha

(10) Patent No.: US 7,738,320 B2
(45) Date of Patent: Jun. 15, 2010

(54) METHOD AND SYSTEM FOR ENHANCED DISPLAY OF TEMPORAL DATA ON PORTABLE DEVICES

(75) Inventor: Basel Hasan Taha, Madison, WI (US)

(73) Assignee: General Electric Co., Schenectady, NY (US)

( * ) Notice: Subject to any disclaimer, the term of this patent is extended or adjusted under 35 U.S.C. 154(b) by 357 days.

(21) Appl. No.: 11/949,265

(22) Filed: Dec. 3, 2007

(65) Prior Publication Data

US 2009/0141593 A1 Jun. 4, 2009

(51) Int. Cl.
G04B 47/00 (2006.01)
G04C 17/00 (2006.01)
G06T 11/20 (2006.01)

(52) U.S. Cl. .................... 368/10; 368/239; 345/440

(58) Field of Classification Search ............... 368/10, 368/82–84, 223, 239–242; 345/23, 440, 345/440.1
See application file for complete search history.

(56) References Cited

U.S. PATENT DOCUMENTS

| | | | |
|---|---|---|---|
| 4,451,157 A * | 5/1984 | Reap | 368/11 |
| 4,626,840 A | 12/1986 | Glasper et al. | |
| 4,694,324 A | 9/1987 | Matney | |
| 4,780,712 A | 10/1988 | Itaya et al. | |
| 4,785,432 A * | 11/1988 | Havel | 368/82 |
| 4,802,106 A | 1/1989 | Saito et al. | |
| 4,995,015 A * | 2/1991 | Chiang | 368/11 |
| 5,008,870 A * | 4/1991 | Vessa | 368/242 |
| 5,216,641 A * | 6/1993 | Hoel | 368/10 |
| 5,363,307 A * | 11/1994 | Yoshida | 701/219 |
| 5,484,205 A * | 1/1996 | Grupp et al. | 374/142 |
| 5,717,879 A | 2/1998 | Moran et al. | |
| 5,838,643 A * | 11/1998 | Reiner | 368/223 |
| 6,259,655 B1 * | 7/2001 | Witort | 368/28 |
| 6,828,981 B2 | 12/2004 | Richardson | |
| 7,035,170 B2 * | 4/2006 | Narayanaswami et al. | 368/223 |
| 7,599,255 B2 * | 10/2009 | Kent | 368/82 |
| 2003/0007420 A1 * | 1/2003 | Shteyn | 368/10 |
| 2005/0132149 A1 | 6/2005 | Hillis et al. | |
| 2005/0190652 A1 * | 9/2005 | Marhic et al. | 368/15 |
| 2007/0237033 A1 * | 10/2007 | Marhic et al. | 368/19 |
| 2008/0062819 A1 * | 3/2008 | Kelly et al. | 368/11 |

* cited by examiner

Primary Examiner—Vit W Miska

(57) ABSTRACT

A method for displaying temporal data on a portable device is presented. The method includes converting the temporal data to clock coordinates to generate a clock data set. In addition, the method includes presenting a clock plot representative of the clock data set on a dial of a clock. Systems and computer-readable medium that afford functionality of the type defined by this method are also contemplated in conjunction with the present technique.

7 Claims, 8 Drawing Sheets

FIG. 3

| X-Coordinate of Temporal Patient Data | Angular Component of Clock Coordinate (in Degrees) | Clock Hour Marking on Clock Dial |
|---|---|---|
| 0 | 0 | 12 |
| 1 | 30 | 1 |
| 2 | 60 | 2 |
| 3 | 90 | 3 |
| 4 | 120 | 4 |
| 5 | 150 | 5 |
| 6 | 180 | 6 |
| 7 | 210 | 7 |
| 8 | 240 | 8 |
| 9 | 270 | 9 |
| 10 | 300 | 10 |
| 11 | 330 | 11 |
| 12 | 360 | 12 | ial data on small display devices, such as cell phones or personal digital assistants (PDAs), thereby enhancing clinical workflow as the clinician may easily visualize a snapshot of relevant patient data.

METHOD AND SYSTEM FOR ENHANCED DISPLAY OF TEMPORAL DATA ON PORTABLE DEVICES

BACKGROUND

This disclosure relates generally to clinical information systems, and more particularly, to systems and methods for displaying temporal data on small mobile devices.

Patient care has become increasingly complex with the widespread use of advanced technologies in routine care. Furthermore, healthcare providers are required to keep track of a staggering amount of information, and their failure to do so may have a detrimental effect on patient care. A solution to this problem may include a Clinical Information System (CIS). As will be appreciated, the CIS may be configured to aid in the acquisition, storage, manipulation, and distribution of clinical information throughout a caregiving facility like a hospital. In other words, the CIS may be employed to collect and store information associated with one or more patients in a caregiving facility. A clinician may then access the stored patient information to monitor a status of the patients and/or to make a diagnosis.

In certain situations, it may be desirable for the clinician to monitor temporal patient data outside the caregiving facility. Advances in digitization of data have allowed the patient data to be available to the clinician outside the caregiving facility. Vital clinical information, once confined to bedside monitors, is becoming easily available to caregivers, such as clinicians, at remote locations with the advent of CIS employing Web portals. In addition, clinicians today have access to patient data in their offices and/or homes. In other words, the clinician may access patient data from his/her home, office, or any other location that is remote from the caregiving facility. More recently, the patient data may also be accessed via a mobile device that has a relatively small display, where the mobile device may include a cell phone, a pager, a personal digital assistant (PDA), or the like.

Furthermore, in certain situations, it may also be desirable for the clinician to monitor temporal patient data outside the caregiving facility. As will be appreciated, the temporal patient data may be representative of patient data acquired over a period of time. For example, temporal clinical data may include patient data such as vital signs like heart rate (HR), blood pressure (BP), blood oxygenation level ($SaO_2$), lab results, or infusion volumes. Moreover, temporal patient data like the heart rate and blood pressure are collected frequently on hospitalized patients and have traditionally been presented graphically as an X-Y time series plot on Clinical Information Systems, thereby allowing the clinician to monitor patient data over an extended period of time.

Moreover, it may also be desirable to view the temporal patient data outside the caregiving facility on a mobile device, such as a cell phone, a pager, or a PDA, for example. However, one of the biggest challenges of displaying temporal patient data on a mobile device, such as a PDA, is an effective display of the temporal patient data on a relatively small display of the PDA. Displaying the time-series data on screen of a PDA or a screen of a cell phone may be visually taxing or may require scrolling. In addition, visualization of temporal data on the display of a mobile device, such as a PDA, a cell phone, or a pager, may disadvantageously result in loss of granularity of data and/or resolution.

It may therefore be desirable to develop a design that allows efficient display of temporal data on a relatively small display of a mobile device. More particularly, there is a need for an approach for efficiently displaying low-density and/or high-density temporal data on small display devices, such as cell phones or personal digital assistants (PDAs), thereby enhancing clinical workflow as the clinician may easily visualize a snapshot of relevant patient data.

BRIEF DESCRIPTION

In accordance with aspects of the present technique, a method for displaying temporal data on a portable device is presented. The method includes converting the temporal data to clock coordinates to generate a clock data set. In addition, the method includes presenting a clock plot representative of the clock data set on a dial of a clock. Computer-readable medium that afford functionality of the type defined by this method is also contemplated in conjunction with the present technique.

In accordance with further aspects of the present technique, a data processing platform is presented. The data processing platform includes a clock plot generating module, where the clock plot generating module is configured to convert temporal data to clock coordinates to generate a clock data set, and present a clock plot representative of the clock data set on a dial of a clock.

In accordance with another aspect of the present technique, a system is presented. The system includes a data storage system configured to store temporal data. Further, the system includes a portable device configured to display the temporal data on a display, where the portable device includes a data processing platform configured to convert the temporal data to clock coordinates to generate a clock data set, and present a clock plot representative of the clock data set on a dial of a clock.

DRAWINGS

These and other features, aspects, and advantages of the present invention will become better understood when the following detailed description is read with reference to the accompanying drawings in which like characters represent like parts throughout the drawings, wherein:

FIG. 3 is a diagrammatic illustration of an exemplary method of converting temporal data to a clock data set, in accordance with aspects of the present technique;

DETAILED DESCRIPTION

As will be described in detail hereinafter, methods and systems for displaying temporal data and/or complex data on a display of a small portable device are presented. Employing the methods and systems described hereinafter, clinical workflow may be dramatically enhanced by allowing a clinician to remotely access and view temporal patient data on a relatively small display of a portable device, such as a cell phone, a PDA, or a pager, for example.

Although, the exemplary embodiments illustrated hereinafter are described in the context of a medical imaging system, it will be appreciated that use of the system in industrial applications are also contemplated in conjunction with the present technique. For example, the exemplary embodiments may be employed to monitor progression of a crack in a gas pipeline or an oilrig.

Figure 1:
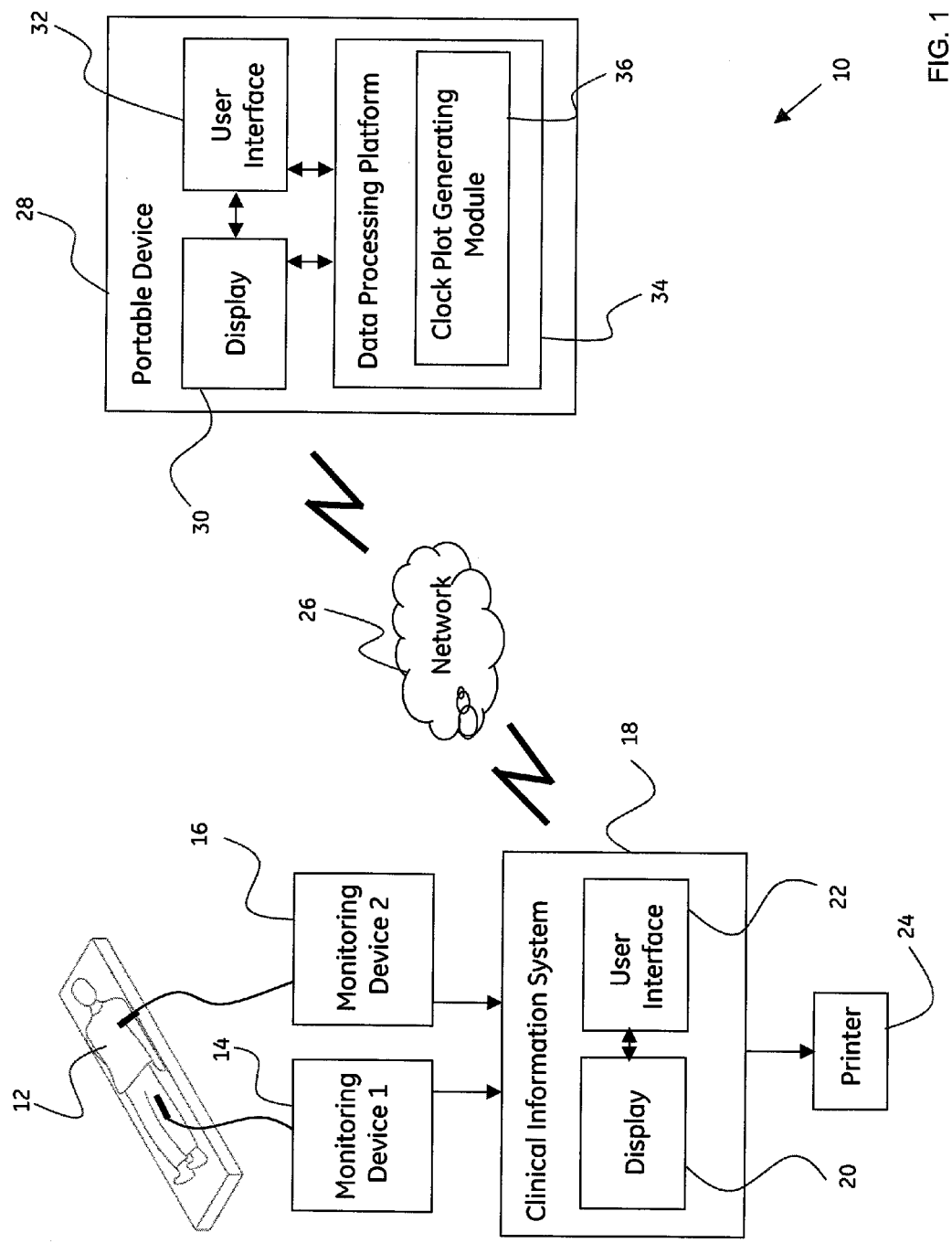
FIG. 1 is a diagrammatic illustration of a diagnostic system, in accordance with aspects of the present technique.

FIG. 1 is a block diagram of an exemplary diagnostic system 10 for use in monitoring a patient 12, in accordance with aspects of the present technique. As will be appreciated by one skilled in the art, the figures are for illustrative purposes and are not drawn to scale. The system 10 may be configured to facilitate acquisition of patient data from the patient 12 via one or more medical devices. In a presently contemplated configuration the one or more medical devices may include one or more monitoring devices. It may be noted that although the embodiments are described hereinafter with reference to monitoring devices, it may be appreciated that use of the present technique with image acquisition devices are also contemplated.

It may be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Furthermore, it should be noted that although the exemplary embodiments illustrated hereinafter are described in the context of a medical imaging system, such as, but not limited to, an ultrasound imaging system, an optical imaging system, a computed tomography (CT) imaging system, a magnetic resonance (MR) imaging system, an X-ray imaging system, or a positron emission tomography (PET) imaging system, other imaging systems, such as, but not limited to, a pipeline inspection system, a liquid reactor inspection system, or other imaging systems are also contemplated in accordance with aspects of the present technique.

In the embodiment illustrated in FIG. 1, the system 10 is illustrated as including a first monitoring device 14 and a second monitoring device 16. Although the present example shows the diagnostic system 10 as including two monitoring devices 14, 16, it may be noted that the system 10 may include one or more monitoring devices. In accordance with further aspects of the present technique, the system 10 may also include one or more imaging systems (not shown in FIG. 1).

The first and second monitoring devices 14, 16 may be operatively coupled to the patient 12. The first and second monitoring devices 14, 16 may include a blood pressure monitor, a heart rate monitor, or a blood oxygen level monitor, for instance. By way of example, the first monitoring device 14 may be configured to obtain a blood pressure of the patient 12 under observation, while the second monitoring device 16 may be configured to facilitate acquisition of a heart rate of the same patient 12.

It may be noted that although the present example illustrates the monitoring devices 14, 16 as being coupled to the patient 12 via cables, it will be understood that the monitoring devices 14, 16 may be coupled to the patient 12 via other means, such as wireless means, for example. Also, in certain other embodiments, patient data may be acquired by the monitoring devices 14, 16 via one or more sensors (not shown) that may be disposed on the patient 12. By way of example, the sensors may include physiological sensors (not shown), such as electrocardiogram (ECG) sensors and/or positional sensors, such as electromagnetic field sensors or inertial sensors. These sensors may be operationally coupled to a data acquisition device, such as a clinical information system (CIS) 18, via leads (not shown), for example.

The system 10 may be configured to monitor data associated with a patient 12, where the patient data may include vital patient parameters. In the present example illustrated in FIG. 1, the patient data may be obtained via the first and second monitoring devices 14, 16. The patient data may include patient parameters such as a temperature, systolic and diastolic blood pressure, a pulse rate, or an oxygen saturation of hemoglobin in arterial blood (a blood oxygen level) ($SpO_2$), to name a few. In other words, the one or more monitoring devices 14, 16 may be configured to monitor different patient vital parameters associated with the patient 12. For example, the blood pressure of a patient 12 may be measured via use of a blood pressure monitor that is operatively coupled to the patient 12, while a thermometer may be used to measure the temperature of the patient 12. Alternatively, a single medical device may be used to measure one or more parameters. By way of example, a pulse oximeter may be used to measure both the $SpO_2$ and the pulse rate of the patient 12. Another example may include a multi-parameter patient monitor which may be configured to simultaneously monitor an electrocardiogram, $SaO_2$, a temperature, and a non-invasive blood pressure (NIBP). The patient data so acquired by the monitoring devices 14, 16 may then be communicated to the CIS 18.

Medical data management systems, such as the CIS 18, have been employed to facilitate organization and management of a variety of data, including patient data, information on procedures and studies that have been scheduled for patients, reports and notes from doctors and technologists relating to procedures and studies, medical images, lab results, billing and insurance information, and many other types of information relevant to medical professionals and management of medical facilities. Different types of medical information may be organized into a workflow, in which the necessary data is passed from one staff member, doctor, group, or department to the next, to assist in providing each staff member with relevant information.

The CIS 18 may be configured to process the patient data acquired via the monitoring devices 14, 16. Additionally, the CIS 18 may include a corresponding display 20 and a user interface 22. The CIS 18 may be configured to provide a visual representation of the patient data on the display 20. A user, such as a clinician, may use the user interface 22 of the CIS 18 to manipulate and/or organize the patient data in the CIS 18. For example, the clinician may use the user interface 22 to alter a display of the patient data on the display 20 of the CIS. Alternatively, the clinician may also facilitate the display of the patient data on the printer 24, for example.

As will be appreciated, the clinician may access the patient information stored in the CIS 18 to monitor a status of the patient and/or to make a diagnosis. Advances in digitization of data have allowed the patient data to be available to the clinician outside the caregiving facility. Vital clinical information, once confined to bedside monitors, is becoming more and more available to caregivers at remote locations with the advent of clinical information systems employing Web portals. Physicians today have access to clinical data in their offices, homes and increasingly on mobile devices, where the mobile devices may include a cell phone, a pager, or a personal digital assistant (PDA), for example. The mobile device may generally be represented by reference numeral 28. It may be noted that the terms mobile device and portable device may be used interchangeably. Accordingly, the system 10 may be configured to communicate the patient data from the CIS 18 to the mobile device 28 via a network 26. In the example illustrated in FIG. 1, the mobile device 28 is shown as including a display 30 and a user interface 32. In addition, the mobile device 28 may also include a data processing platform 34, where the data processing platform 34 may be configured to aid in displaying temporal patient data on the relatively small display 30 of the mobile device 28. In a presently contemplated configuration, the data processing platform 34 may include a clock plot generating module 36, where the clock plot generating module 36 may be configured to aid processing the temporal patient data for display on the relatively small display 30 of the mobile device 28. The working of the data processing platform 34 and the clock plot generating module 36 will be described in greater detail with reference to FIGS. 2-8.

As will be appreciated, in certain situations, it may be desirable for the clinician to monitor temporal patient data, where the temporal clinical data may include patient data, such as, but not limited to, vital signs like heart rate, blood pressure, or a blood oxygenation level. It may be noted that the terms temporal clinical data and temporal patient data may be used interchangeably. Traditionally, the temporal patient data is collected frequently from hospitalized patients and are presented graphically as an X-Y time series plot in clinical information systems, such as the CIS 18. However, efficiently displaying the temporal patient data on a relatively small display, such as the display 30 of the mobile device 28, is an onerous task, as the visualization of temporal patient data typically entails the use of a relatively large (wide) display device such as a standard computer monitor. Additionally, viewing temporal patient data on the small display 30 of the mobile device 28 may be visually taxing and require scrolling, as previously noted.

Figure 2:
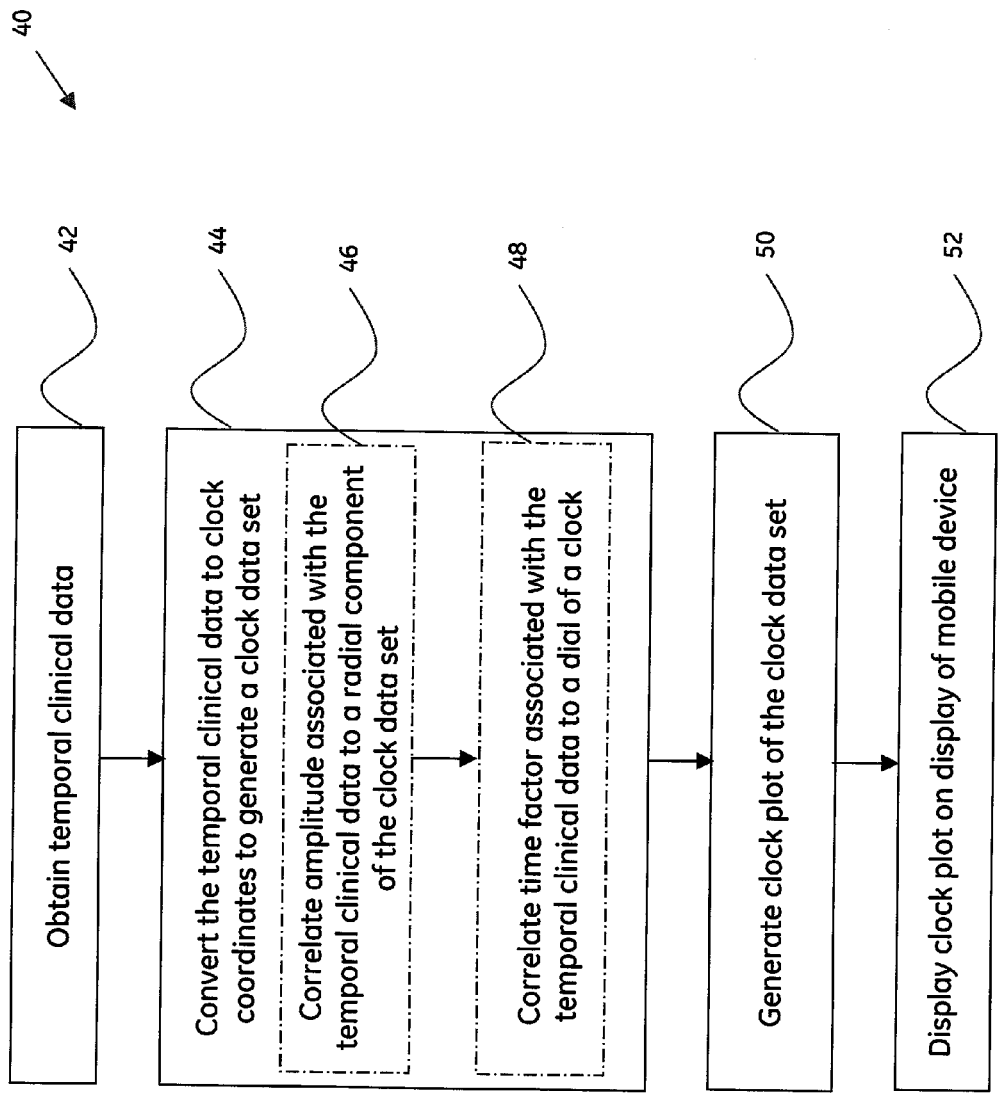
FIG. 2 is a flow chart illustrating an exemplary process of displaying temporal data on a display of a small portable device, in accordance with aspects of the present technique.

Accordingly, a method of efficiently displaying temporal patient data on the relatively small screen 30 of the mobile device 28, such as a PDA, is presented. More particularly, the method presents a technique of efficiently displaying the temporal patient data on the display 30 of the mobile device 28. FIG. 2 illustrates a flow chart 40 of the method of displaying temporal clinical data on a display of a mobile device, such as the mobile device 28 (see FIG. 1).

The method starts at step 42 where the mobile device 28 may be configured to obtain temporal patient data representative of one or more patient parameters. The mobile device 28 may be configured to obtain the temporal patient data from the clinical information system 18 (see FIG. 1), for example. As noted hereinabove, visualization of temporal patient data on a display of a mobile device employing currently available techniques typically may be visually taxing and/or require scrolling. In accordance with exemplary aspects of the present technique, the shortcomings of the currently available techniques may be circumvented by presenting the temporal patient data in a clock plot "mimicking" a dial of a clock. In other words, the temporal patient data may be converted to a corresponding data set in clock coordinates. As used herein, the term clock plot may be used to refer to a data plot, where the data has been plotted on a dial of a clock. Also, as used herein, the term clock coordinates may be used to refer to coordinates associated with the clock plot. More particularly, the data set in clock coordinates may include a radial component r and an angular component θ, where the angular component θ may be representative of hour markings on a clock dial.

In accordance with exemplary aspects of the present technique, the temporal patient data may be presented as a clock plot mimicking a dial of a clock. Accordingly, at step 42, the temporal patient data associated with a twelve-hour period may be obtained, where each hour corresponding to the temporal patient data may be correlated to a corresponding hour on the clock dial. More particularly, a mobile device, such as the mobile device 28 (see FIG. 1), may be configured to obtain the temporal patient data corresponding to the 12-hour period from a data storage, such as the CIS 18 (see FIG. 1). In one embodiment, the mobile device 28 may obtain the temporal patient data from the CIS 18 over a network, such as the network 26 (see FIG. 1). Also, in accordance with aspects of the present technique, temporal patient data corresponding to a twelve hour period from about 12:01 a.m. to about 12:00 noon may be selected. This time period from about 12:01 a.m. to about 12:00 noon may be referred to as an "AM" period. Alternatively, temporal patient data corresponding to another 12-hour period from about 12:01 p.m. to about 12:00 midnight may be selected. This time period from about 12:01 p.m. to about 12:00 midnight may be referred to as a "PM" period. It may be noted that other twelve-hour periods may also be selected. For example, a time period from about 10:00 a.m. to about 10:00 p.m. may also be selected.

Once the temporal patient data corresponding to a selected 12-hour time period is obtained, the temporal patient data may be converted to a data set in corresponding clock coordinates, as indicated by step 44. In accordance with aspects of the present technique, a radial component r of the patient data in clock coordinates may be computed using:

$$r = y \tag{1}$$

where y may be representative of a Y-coordinate of the temporal patient data. In certain embodiments, the Y-coordinate may include an amplitude of a data signal, such as a blood pressure.

Similarly, an angular component θ of the clock data may be computed using:

$$\theta = \left(\frac{x\pi}{6}\right) \tag{2}$$

where x may be representative of an X-coordinate of the temporal patient data. In certain embodiments, the X-coordinate may be indicative of a time factor associated with the data signal.

Accordingly, at step 44, equations (1) and (2) may be employed to convert the temporal patient data to a corresponding clock data set or a data set in clock coordinates. More particularly, an amplitude (Y-coordinate) of the temporal patient data may be converted to a corresponding radial component r of the clock data set employing equation (1), as indicated by step 46. The data processing platform 34 (see FIG. 1) may be configured to facilitate the conversion of the amplitude of the temporal patient data set to a radial component of the clock data set.

Additionally, the time factor (X-coordinate) of the temporal patient data may be converted to a corresponding angular component θ of the clock data set using equation (2), as depicted by step 48. In other words, a time factor associated with the temporal patient data may be correlated to the dial of a clock. Here again, the data processing platform 34 may be configured to facilitate the correlation of the time associated with the temporal patient data set to a corresponding hour on the clock dial.

It may be noted that in a presently contemplated configuration, a 12-hour marking on the dial of the clock may be representative of an initial value of an angular component θ of the data in clock coordinates. In other words, the "12" hour marking on the clock dial may be representative of an angular component of about "0" degrees. Further, a value of the angular component θ may be configured to increase in a clockwise direction on the clock dial. Accordingly, each hour marking on the clock dial may be separated by about 30 degrees. For example, the "1" hour marking on the clock dial may be located at about 30 degrees from the "12" hour (0 degree) marking, while the "6" hour marking on the clock dial may be located at about 180 degrees from "12" hour marking. The correspondence between the X-coordinate of the temporal patient data and the angular component θ of the clock coordinates as determined by equation (2) may be summarized in Table. 1 (see FIG. 3).

Turning now to FIG. 3, an example 54 of correspondence between the temporal patient data and a corresponding data set in clock coordinates using equation (2) is illustrated. Reference numeral 56 may be representative of an X-coordinate of the temporal patient data. In the present example, the X-coordinate may include the time factor, ranging for example from "0" hours to "12" hours. Similarly, reference numeral 57 may be representative of an angular component θ of the data set in clock coordinates that is computed using equation (2). Furthermore, reference numeral 58 may be indicative of an hour marking on the clock dial, where the hour marking corresponds to an angular component θ of the clock coordinates. By implementing the angular component θ of the clock data as indicated by equation (2), the X-coordinate of the temporal patient data, namely the time factor, may be easily associated with a corresponding hour marking on the dial of the clock. More particularly, each hour in the 12-hour time period corresponding to the temporal patient data may be correlated to an hour on a clock dial. For example, the temporal patient data acquired at 10:00 am may be correlated to the "10" hour marking on the clock dial.

Following the conversion of the temporal patient data to the corresponding data set in clock coordinates, a clock plot of the patient data in clock coordinates corresponding to the selected 12-hour period may be generated, as depicted by step 50. For example, clock data corresponding to the temporal patient data collected over a time period between 1:00 a.m. and 2:00 a.m. may be represented in a sector between the "1" and "2" hour markings on the clock dial. In other words, data in clock coordinates corresponding to the temporal patient data in the 1:00 a.m. to 2:00 a.m. time period may be plotted in the sector between the "1" and "2" hour markings on the clock dial. Accordingly, a clock plot may be generated using the clock data set that corresponds to the temporal patient data acquired over the 12-hour period. In other words, the clock plot may be generated such that the radial component of the clock data set may be plotted along a corresponding hour (radial line) of the clock dial. The data processing platform 34, and more particularly the clock plot generating module 36 (see FIG. 1) may be configured to facilitate the generation of the clock plot. Subsequently, at step 52, the generated clock plot may be displayed on the display 30 (see FIG. 1) of the mobile device 28. Here again, the data processing platform 34 may be configured to aid in displaying the generated clock plot on the display 30 of the mobile device 28.

In accordance with further aspects of the present technique, a clinician operating the mobile device 28 may be allowed to select one or more patients. Temporal patient data corresponding to the selected patient(s) may be obtained. Subsequently, clock plots corresponding to temporal patient data associated with the selected patient(s) may be generated and displayed mimicking the clock dial. These clock plots may then be visualized on the display 30 of the mobile device 28.

Additionally, the method may be configured to also allow the clinician to select a desired time period for visualization of corresponding clinical data. For example, the clinician may select a morning period ("AM") or an evening period ("PM"). The mobile device 28 may then obtain temporal patient data corresponding to the selected time period. Here again, clock plots corresponding to temporal patient data associated with the selected time period may be generated and displayed mimicking the clock dial. Subsequently, these clock plots may be visualized on the display 30 of the mobile device 28.

Moreover, the method may also be configured to allow the clinician to select a date corresponding to a desired set of temporal patient data to be visualized. By way of example, it may be desirable for the clinician to view the temporal patient data acquired the previous day during a corresponding time period. Once the desired date is selected, the corresponding temporal data set may be acquired, and clock plots may be generated and displayed mimicking the clock dial. These clock plots may be visualized on the display of the mobile device.

Additionally, the method may also be configured to allow the clinician to select one or more patient parameters. In other words, the clinician may select one or more patient parameters. Temporal patient data corresponding to the selected patient parameters may be obtained by the mobile device 28. Subsequently, clock plots corresponding to the selected parameters may be generated and displayed mimicking the clock dial on the display 30 of the mobile device 28.

Implementing the method of displaying temporal patient data as described hereinabove, advantageously allows clinicians to access and efficiently view clinical data on a relatively small display of a mobile device, such as a cell phone, a pager, or a PDA. In addition, the clock plot of the clinical data mimics the familiar dial of a clock, thereby making the correlation of the clinical data to time substantially natural and relatively easy. Furthermore, the clinician may select one or more parameters to be visualized. Moreover, the clock plot allows the clinician to efficiently to view up to 12 hours worth of clinical data within the relatively small size of the display of the mobile device.

Figure 4:
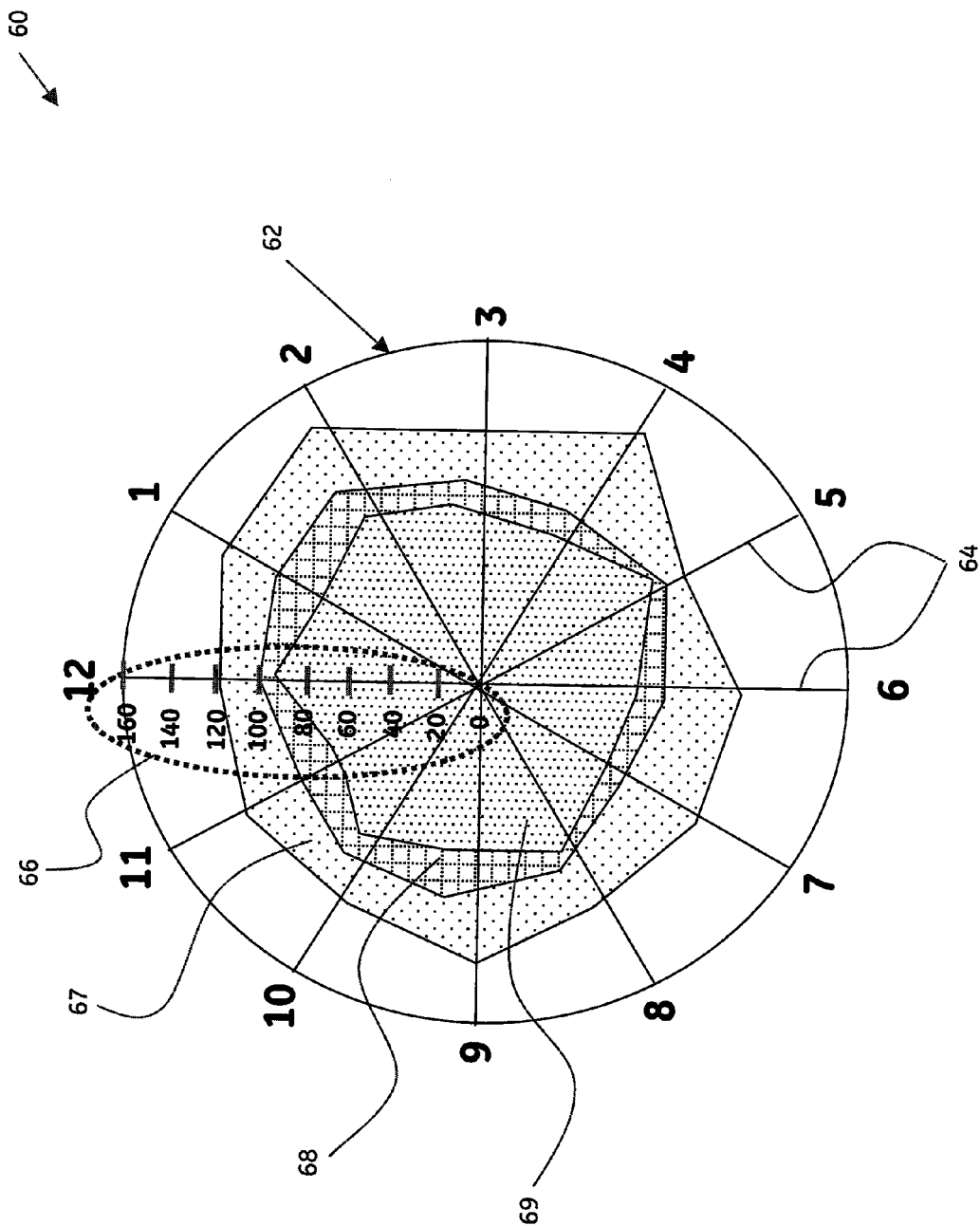
FIG. 4 is a diagrammatic illustration of an exemplary method of displaying temporal data on a clock dial, in accordance with aspects of the present technique.

The method of displaying temporal patient data described with reference to FIG. 2 may be better understood with reference to FIG. 4. Turning now to FIG. 4, a diagrammatic illustration 60 of an exemplary clock plot mimicking a clock dial 62 is illustrated. Reference numeral 64 may be representative of radial lines that are indicative of the "hour" markings on the clock dial 62. Furthermore, each radial line 64 may be labeled with a plurality of values, wherein the plurality of values may be representative of different values of a radial component of a clock data set. These values may generally be represented by reference numeral 66. By way of example, if the clinician desires to view a blood pressure of the patient monitored over a period of 12 hours, then the radial lines 64 may be labeled with different values of units used to measure blood pressure, namely mm/Hg. Similarly, the radial lines 64 may be labeled with different values of units representative of heartbeats per minute if the clinician is desirous of viewing a pulse rate of the patient.

In the example illustrated in FIG. 4, clock plots of a blood pressure of a patient acquired over a 12-hour period are depicted. Reference numeral 67 may be representative of a clock plot of systolic blood pressure of the patient, while a clock plot representative of diastolic blood pressure of the patient may generally be represented by reference numeral

69. In addition, reference numeral 68 may be indicative of a clock plot of a mean average blood pressure of the patient. It may be noted that the clock plots 67, 68, 69, may be representative of clinical data acquired over a 12-hour period. By representing the temporal patient data as clock plots on the familiar clock dial 62, the clinician may easily view a snap shot of the patient data acquired over a 12-hour period. More particularly, the clinician need not scroll to view the entire set of clinical data. Also, the clinician may advantageously view a variation of the clinical data over the 12-hour period. For example, the clinician may easily observe that the systolic blood pressure has a value of about 120 mm/Hg at about 1:00 a.m., and a value of about 100 mm/Hg at about 5:00 a.m. In a similar fashion, the diastolic blood pressure at 1:00 a.m. has a value of about 90 mm/Hg, and a value of about 85 mm/Hg at about 5:00 a.m. Additionally, the mean average blood pressure has a value of about 105 mm/Hg at about 1:00 a.m. and a value of about 93 mm/Hg at about 5:00 a.m.

In accordance with further aspects of the present technique, clock plots corresponding to more than one parameter may be simultaneously displayed on the clock dial 62. For example, although the example illustrated in FIG. 4 illustrates clock plots corresponding to a single parameter, namely the blood pressure, clock plots corresponding to other parameters may also be simultaneously displayed on the clock dial 62. It may be noted that in order to facilitate effective simultaneous display of more than parameter, it may be desirable for the one or more parameters to have substantially similar units of measurement.

Figure 5:
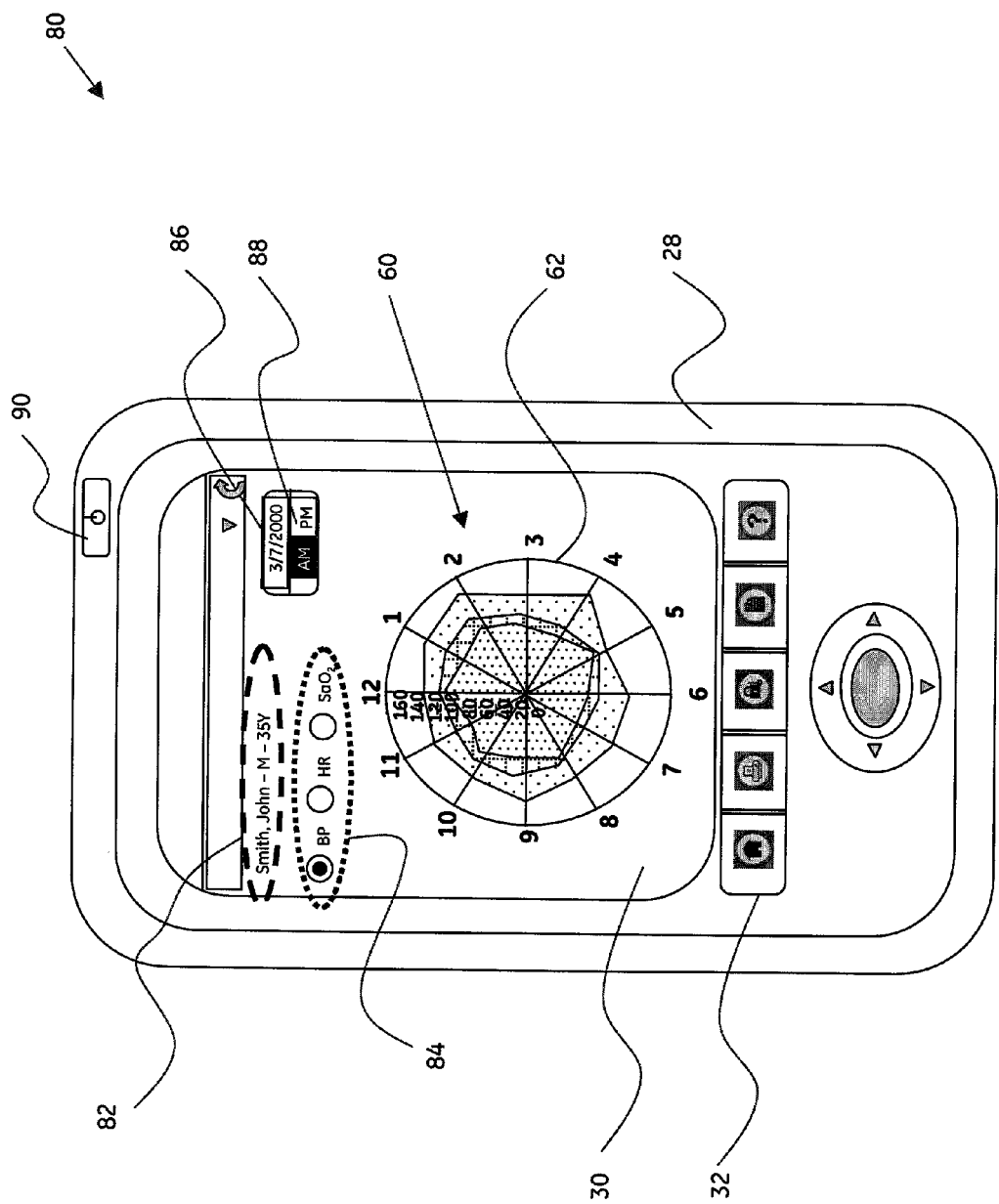
FIG. 5 is a diagrammatic illustration of an exemplary method of displaying temporal data on a display of a portable device, in accordance with aspects of the present technique.

Referring now to FIG. 5, a diagrammatic illustration 80 of a portable device, such as the mobile device 28 (see FIG. 1), configured to view temporal data, in accordance with aspects of the present technique is depicted. More particularly, the temporal patient data may be presented as a clock plot, such as the clock plots 67, 68, 69 (see FIG. 4), on a clock dial, such as the clock dial 62 (see FIG. 4) as described with reference to FIGS. 2-4.

As previously noted, a clinician operating the mobile device 28 may be allowed to select one or more patients. In a presently contemplated configuration, the clinician may select the desired patient(s) via a patient field 82. Once the desired patient is selected, temporal patient data corresponding to the selected patient(s) may be obtained. Clock plots corresponding to temporal patient data associated with the selected patient(s) may be generated and displayed mimicking the clock dial. In addition, these clock plots may then be visualized on a display, such as the display 30 (see FIG. 1) of the mobile device 28.

Furthermore, the clinician may select one or more patient parameters. In other words, the clinician may select one or more patient parameters and view a corresponding data set on the clock dial 62. In a presently contemplated configuration, the clinician may select the one or more patient parameters via a parameter field 84. In the example illustrated in FIG. 5, the parameter field 84 is shown as including 3 radio buttons corresponding to a blood pressure, a heart rate, and a blood oxygenation level. However, in other embodiments, more than 3 parameters may be displayed on the display 30 of the mobile device 28. For example, the parameters may be provided in a drop down menu, thereby allowing the clinician a wider choice of patient parameters to select from. Temporal patient data corresponding to the selected patient parameters may be obtained by the mobile device 28. Subsequently, clock plots corresponding to the selected parameters may be generated and displayed mimicking the clock dial on the display 30 of the mobile device 28.

Moreover, the mobile device 28 may also be configured to allow the clinician to access clinical data from a different day. In other words, the clinician may view patient data corresponding to a date that is different from a current date. Accordingly, the clinician may select the desired date via use of a date field 86. In certain embodiments, once the clinician selects the date field 86, the mobile device 28 may be configured to display a calendar that allows the clinician to select the desired date. Once the desired date is selected, temporal patient data corresponding to the selected date may be acquired, and clock plots may be generated and displayed mimicking the clock dial. These clock plots may be visualized on the display 30 of the mobile device 28.

Additionally, the clinician may also select a desired time frame to view the clinical data via a time frame field 88. More particularly, using the time frame field 88, the clinician may select either an "AM" time frame (12:01 a.m. to 12:00 noon) or a "PM" time frame (12:01 p.m. to 12:00 midnight). By way of example, it may be desirable for the clinician to view the temporal patient data acquired the previous day during a corresponding time period. The mobile device 28 may then obtain temporal patient data corresponding to the selected time period. Here again, clock plots corresponding to temporal patient data associated with the selected time frame may be generated and displayed mimicking the clock dial. Subsequently, these clock plots may be visualized on the display 30 of the mobile device 28. Reference numeral 90 may be representative of a power button on the mobile device 28.

The method of displaying temporal data on a clock dial described hereinabove entails displaying temporal data on a standard 12-hour analog style clock display. In accordance with further aspects of the present technique, the method of displaying temporal data on a clock dial may also be employed to display temporal data on analog-style clock displays that cover time periods other than a 12-hour time period. For example, the other clock displays may include a 24-hour analog-style clock. As will be appreciated, in a 24-hour clock, the hour hand goes round once a day, while the minute and second hands operate as usual. Moreover, modern 24-hour analog clocks use the 24-hour time system, in which the 24 hours of the day are numbered from 1 to 24. In other words, the first 12 hours of the day are numbered from 1 to 12, while the other 12 hours are numbered from 13 to 24. Use of the 24-hour clock dial may advantageously find application in the healthcare environment. By way of example, the clinician may wish to monitor temporal patient data over the course of a full day (24 hours). Accordingly, temporal patient data corresponding to a 24-hour period may be displayed on the 24-hour clock dial, in accordance with aspects of the present technique.

Other examples of clock dials may include an 8-hour clock dial or a 10-hour clock dial, where the 8-hour and/or 10-hour clock dials may be configured to correlate to a standard shift of a worker, such as a clinician or a nurse, for instance. In other words, the nurse or the clinician may wish to monitor temporal patient data during his/her shift. Accordingly, temporal patient data corresponding to the 8-hour and/or 10-hour shift of the nurse may be displayed on a corresponding 8-hour and/or 10-hour clock dial.

Additionally, the method of displaying temporal data on a clock dial may also be used to display financial data on the clock dial, in accordance with further aspects of the present technique. As will be appreciated, financial data, such as stock prices, are typically displayed using X-Y time series plots. The X-axis in the time series plot may be indicative of different time periods, such as the time period of a single trading session, 5 days, 3 months, 6 months, 1 year, or 5 years, for example. The method of displaying temporal data described hereinabove may be employed to display the financial data on the clock dial, thereby allowing stock traders monitor stock prices using their cell phones, pagers, or PDAs.

Furthermore, in accordance with further aspects of the present technique, an enhanced display of temporal data over the previous 12-hour period, for example, on a clock dial may be provided. In one embodiment, the "12" o'clock position of a standard analog-style clock display may always be used to display the present temporal data, with the last 12 hours of data displayed using the clock plot. An application for this type of enhanced display may include a sonar plot generated by a ship searching for a shipwreck on the bottom of a body of water. As will be appreciated, the captain of the ship may typically view a X-Y time series plot in the wheelhouse of the ship. Using the method of displaying temporal data on a clock dial, the captain may use his/her cell phone or PDA to efficiently monitor the search results from locations that are remote from the wheelhouse.

Figure 6:
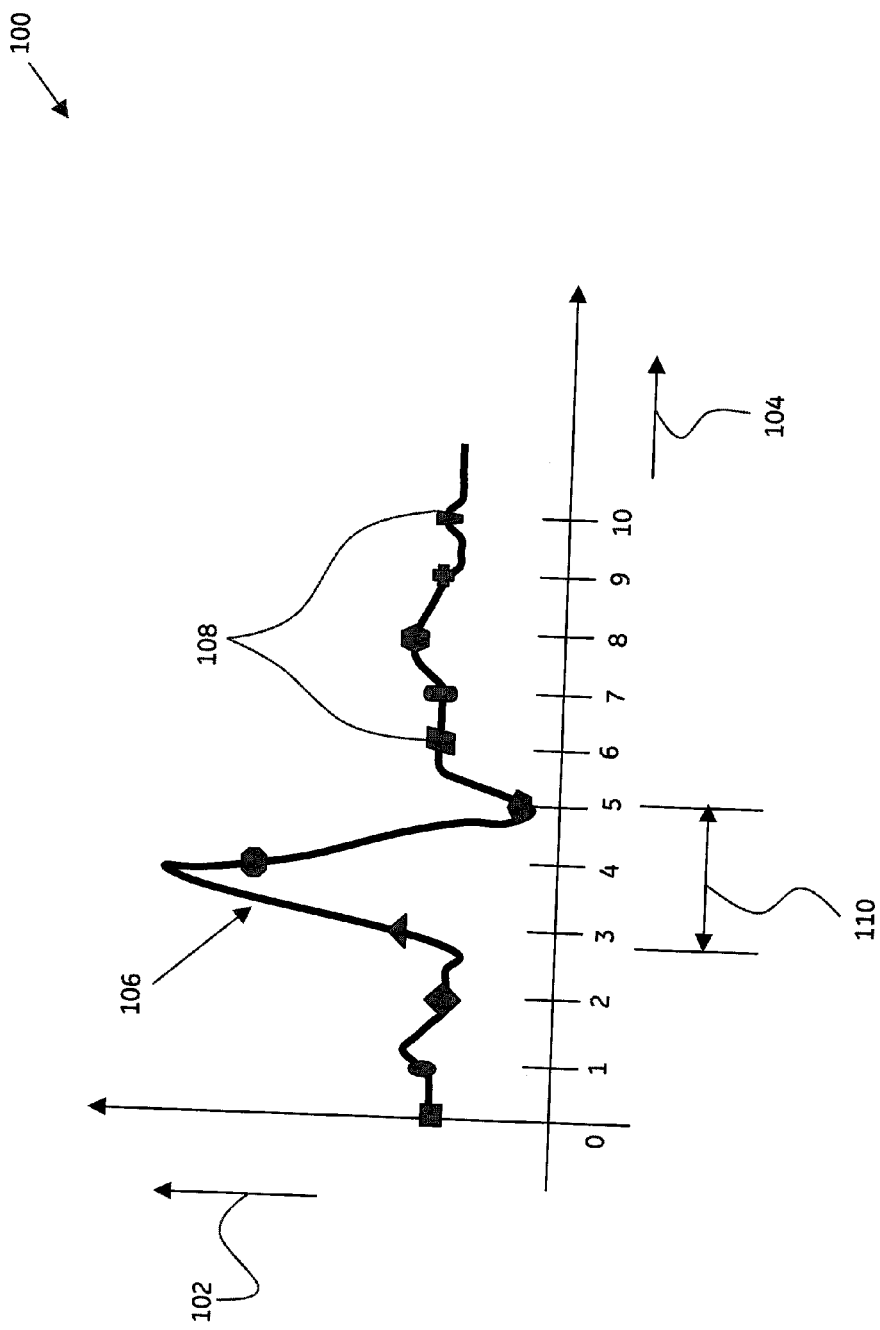
FIGS. 6-7 are diagrammatic illustrations of a method of displaying complex temporal data on a clock dial, in accordance with aspects of the present technique.

In accordance with yet another aspect of the present technique, complex data, such as, but not limited to, biomedical signals, such as signals obtained via a multi-lead electrocardiogram (ECG), may also be displayed on a clock dial. The multi-lead ECG may include a 12-lead ECG, for example. More particularly, the complex clinical data may be displayed on the clock dial via use of a color scale rendition of amplitudes on radial lines of the clock dial, such as the radial lines 64 (see FIG. 4). The method of displaying the complex clinical data may be better understood with reference to FIGS. 6-8. Referring now to FIG. 6, a diagrammatical representation 100 of an ECG signal is depicted. Reference number 102 may be representative of an amplitude of the ECG signal, while a time factor associated with the ECG signal may generally be represented by reference numeral 104.

According to aspects of the present technique, a snapshot of the ECG signal having a predetermined time period may be considered. In one embodiment, a 10-second snapshot of the ECG signal may be considered. More particularly, a 10-second snapshot of the ECG signal about each minute of the hour may be obtained. In the present example, an ECG signal may be representative of a 10 second snapshot obtained about an hour, such as 1:00 p.m., for example. This snapshot of the ECG signal may generally be represented by reference numeral 106. An amplitude value of the ECG signal 106 at each second may be obtained. Subsequently, the amplitude value at each second may be color-coded based on a value of the amplitude. Alternatively, the amplitude value may be indicated via use of a predetermined symbol. In the example illustrated in FIG. 6, the amplitude value at each second may be represented by a symbol corresponding to that amplitude value. Symbols representative of the amplitude values at each second may generally be represented by reference numeral 108. Also, a QRS complex of the ECG signal 106 may generally be represented by reference numeral 110.

Figure 7:
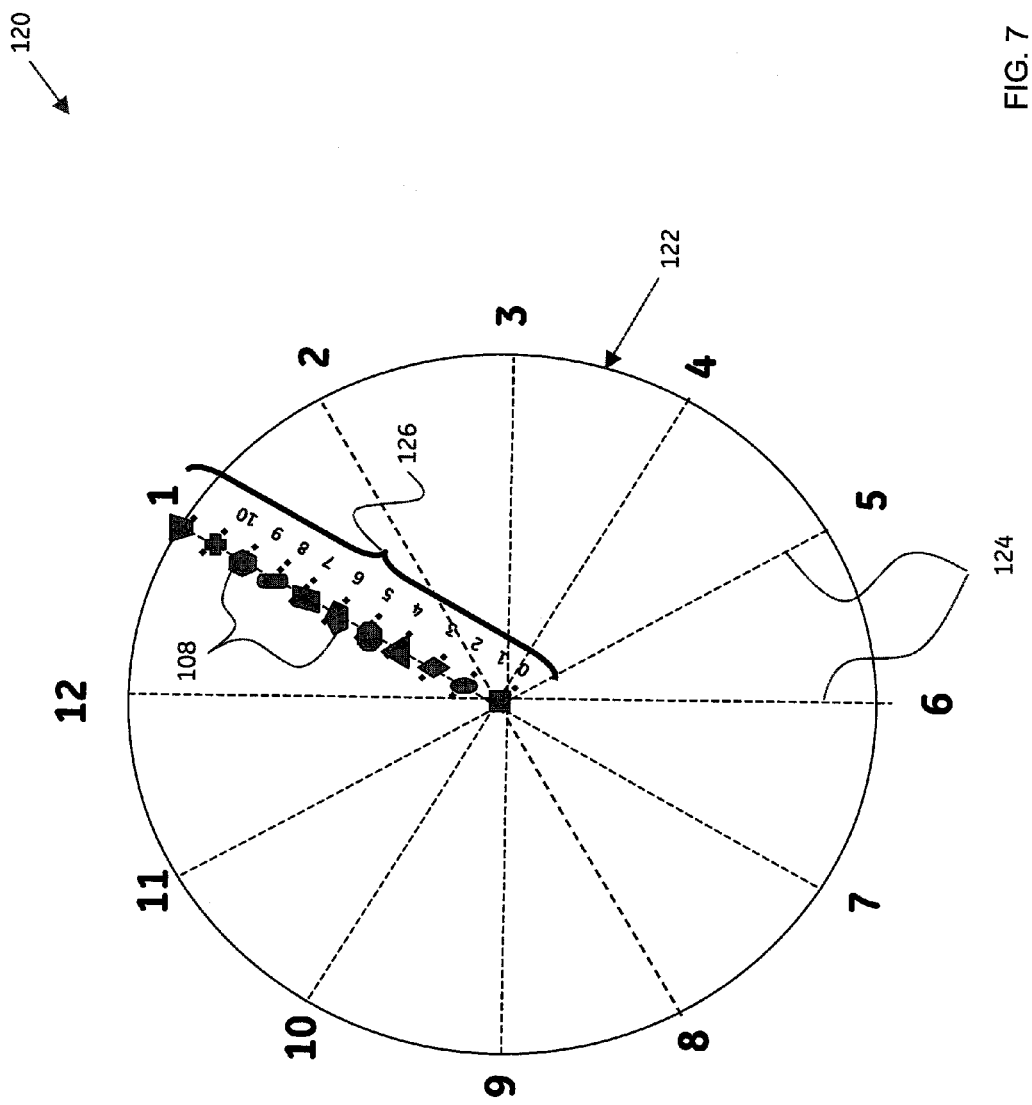

In accordance with exemplary aspects of the present technique, once the amplitude values (symbols 108) at each second of the 10-second snapshot of the ECG signal 106 are obtained, these symbols 108 may be represented on a clock dial. Turning now to FIG. 7, a diagrammatical illustration 120 of an exemplary method of displaying complex data on a clock dial 122 is illustrated. Reference numeral 124 may be representative of radial lines that are indicative of the "hour" markings on the clock dial 122. Furthermore, each radial line 124 may be sub-divided into N sub-divisions, where each sub-division may be representative of 1 second. In accordance with the example illustrated in FIG. 6, each radial line 124 may be sub-divided into 10 sub-divisions as the ECG signal 106 (see FIG. 6) is representative of a 10-second snapshot of an ECG signal about an hour, such as 1:00 p.m. Reference numeral 126 may be representative of these sub-divisions. Subsequently, each symbol 108 (see FIG. 6) may be positioned at a corresponding sub-division 126. Alternatively, these symbols 108 may be color-coded and these colors may be represented on the radial line 124. As previously noted, in the example illustrated in FIG. 7, a 10-second snapshot of the ECG signal 106 around 1:00 p.m. is depicted. In other words, the entire 10-second snapshot of the ECG signal 106 may be represented along a corresponding radial line 124, namely, the radial line corresponding to 1:00 p.m.

This process may be repeated for all the hours in the 12-hour time frame of the clock dial 122. In other words, a 10-second snapshot of the ECG signal may be obtained about each of the 12 hours in the 12-hour time frame of the clock dial 122. In accordance with further aspects of the present technique, the process described hereinabove may also be repeated for each minute marking (not shown in FIG. 7) on the clock dial 122. By implementing the method of displaying complex data on the clock dial 122 as described hereinabove, clinical workflow may be dramatically improved as the clinician may easily trace how far the QRS complex 110 (see FIG. 6) of the ECG signal 106 has progressed, thereby enabling the clinician to take measures to proactively treat any ailments.

Figure 8:
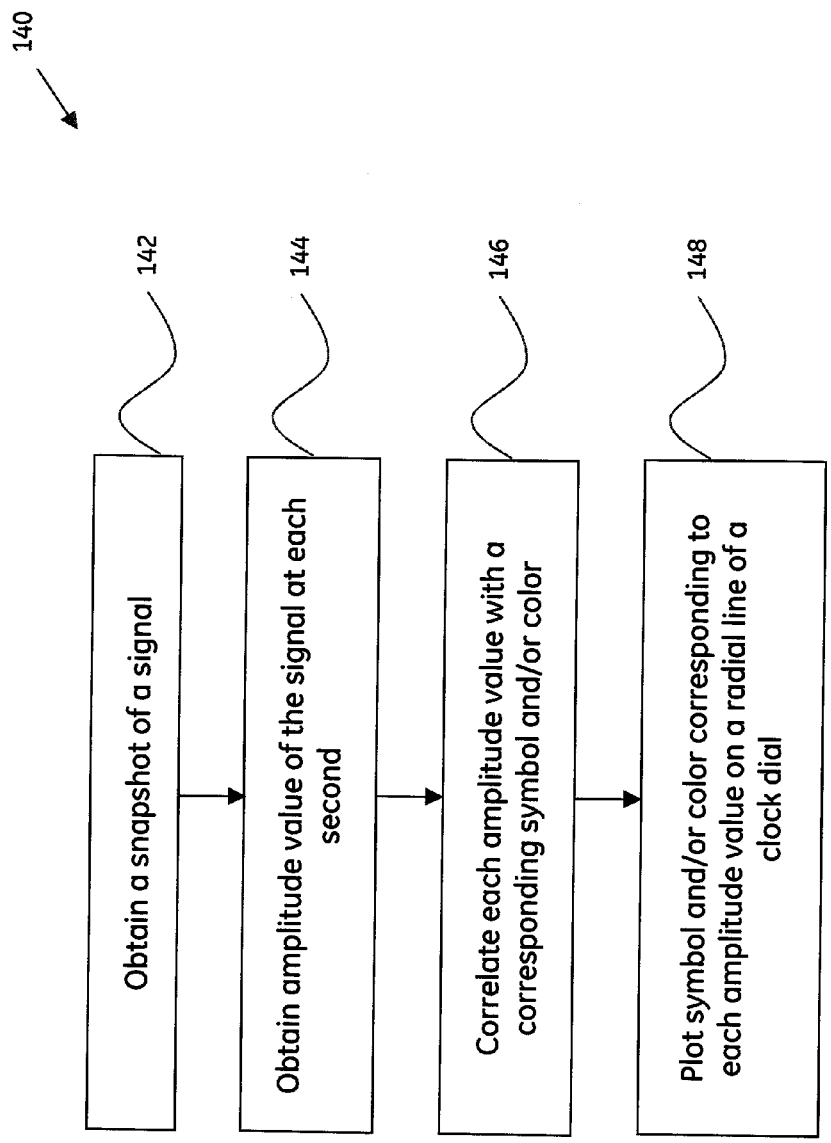
FIG. 8 is a flow chart illustrating an exemplary method of displaying complex temporal data on a display of a small portable device, in accordance with aspects of the present technique.

FIG. 8 is a flow chart 140 illustrating an exemplary method of displaying complex data on a dial of a clock. In accordance with aspects of the present technique, an exemplary method of displaying complex data, such as a 12-lead ECG signal, on the dial of the clock, is presented. The method starts at step 142 where a snapshot of a complex signal, such as the 12-lead ECG signal may be obtained. In one embodiment, a 10-second snapshot of the ECG signal may be obtained. More particularly, the 10-second snapshot of the ECG signal may be obtained around an hour marking on the clock dial 122. For example, a 10-second snapshot of the ECG signal may be obtained at around 1:00 p.m. Subsequently, at step 144, amplitude values of the ECG signal at each second of the 10-second time interval may be obtained. These amplitude values may then be correlated to a corresponding color in a color-coded scheme, as depicted by step 146. Alternatively, at step 146, each amplitude value may be correlated to a corresponding symbol representative of that amplitude value. Furthermore, at step 148, the symbols and/or colors corresponding to these amplitude values may be placed on a corresponding hour marking of the clock dial. By way of example, the symbols and/or colors representative of these amplitude values may be depicted along the 1:00 p.m. radial line on the clock dial. Steps 142-148 may be repeated for each hour of the 12-hour time period. Additionally, steps 142-148 may also be repeated for each minute on the clock dial.

The system for displaying temporal data and the method of displaying temporal data described hereinabove dramatically simplify clinical workflow by advantageously allowing display of low-density and/or high-density temporal patient data on relatively small displays of mobile devices, such as cell phones, pagers, or PDAs, thereby allowing the clinician to easily and efficiently visualize temporal data. More particularly, the temporal data is presented as a "clock" plot mimicking the familiar dial of a clock, thereby allowing the clinician to efficiently correlate the clinical data to time. Additionally, the clinician may view clinical data acquired over a 12-hour period in a single snap shot on a relatively small screen of the mobile device. Moreover, simple controls enable the clinician to select the patient, the parameter to plot, the date, and the time frame (AM or PM). Also, by allowing the clinician to view patient data on a display of a mobile device, clinical workflow may be enhanced as the present technique may be configured to extend the reach of clinical data beyond the clinical setting. In addition, complex clinical data, such as biomedical signals may also be efficiently displayed on the display of the mobile device.

The above-description of the embodiments of the system for displaying temporal data and the method of displaying temporal data have the technical effect of effectively displaying temporal data on a relatively small display of a mobile device, thereby substantially enhancing the clinical workflow and productivity of the caregivers and patient care.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for displaying complex temporal data on a portable device, the method comprising:
    obtaining a snapshot signal of the complex data, wherein the snapshot signal of the complex data comprises a signal representative of the complex data over a predetermined time period, and wherein the predetermined time period comprises a plurality of sub-intervals;
    obtaining amplitudes values of the snapshot signal at each of the plurality of sub-intervals;
    correlating each amplitude value to a predetermined color, a predetermined symbol, or both; and
    generating a plot by plotting the predetermined color, the predetermined symbol, or both, on a corresponding radial line of a dial of a clock.

2. The method of claim 1, further comprising displaying the generated plot on a display of the portable device.

3. The method of claim 1, wherein the step of obtaining a snapshot signal of the complex data includes obtaining a snapshot signal of complex biomedical data.

4. The method of claim 3, wherein the complex biomedical data comprises electrocardiogram (ECG) data.

5. The method of claim 4, wherein each sub-interval is representative of one second, and the amplitude values correspond to the amplitudes of the ECG data at the one-second sub-intervals.

6. The method of claim 1, wherein the corresponding radial line of the dial of the clock on which the plot is generated corresponds to the time of day when the snapshot signal of the complex data was obtained.

7. The method of claim 6, wherein the dial of the clock has a 12-hour time frame.

\* \* \* \* \*